(12) United States Patent
Baril et al.

(10) Patent No.: US 11,246,613 B2
(45) Date of Patent: Feb. 15, 2022

(54) ACTUATION MECHANISMS FOR TISSUE SPECIMEN RETRIEVAL DEVICES AND TISSUE SPECIMEN RETRIEVAL DEVICES INCORPORATING THE SAME

(71) Applicant: Covidien LP, Mansfield, MA (US)

(72) Inventors: Jacob C. Baril, Norwalk, CT (US); Saumya Banerjee, Hamden, CT (US)

(73) Assignee: Covidien LP, Mansfield, MA (US)

( * ) Notice: Subject to any disclaimer, the term of this patent is extended or adjusted under 35 U.S.C. 154(b) by 15 days.

(21) Appl. No.: 16/875,031

(22) Filed: May 15, 2020

(65) Prior Publication Data
US 2021/0353315 A1    Nov. 18, 2021

(51) Int. Cl.
*A61B 17/221*  (2006.01)
*A61B 17/29*   (2006.01)

(52) U.S. Cl.
CPC ........ *A61B 17/221* (2013.01); *A61B 17/2909* (2013.01); *A61B 2017/2212* (2013.01); *A61B 2017/2925* (2013.01)

(58) Field of Classification Search
CPC .. A61B 2017/00287; A61B 2017/2212; A61B 2017/00867; A61B 2017/2215; A61B 2017/2927; A61B 2017/00353; A61B 2017/00477; A61B 2017/320064; A61B 2017/00367; A61B 2017/22034; A61B 17/00234; A61B 17/221; A61B 17/32056; A61B 17/0218; A61B 17/22031; A61B 17/29; A61B 17/3421; A61B 17/320725; A61B 17/00; A61B 17/3417; A61B 2018/1407; A61B 2018/141; A61B 18/1492; A61B 18/1482; A61B 10/02; A61B 10/0266; A61B 10/04
See application file for complete search history.

(56) References Cited

U.S. PATENT DOCUMENTS

| | | | |
|---|---|---|---|
| 6,059,793 | A  | 5/2000  | Pagedas |
| 6,156,055 | A  | 12/2000 | Ravenscroft |
| 6,162,209 | A  | 12/2000 | Gobron et al. |
| 6,171,317 | B1 | 1/2001  | Jackson et al. |
| 6,206,889 | B1 | 3/2001  | Bennardo |
| 6,224,612 | B1 | 5/2001  | Bates et al. |
| 6,228,095 | B1 | 5/2001  | Dennis |
| 6,248,113 | B1 | 6/2001  | Fina |
| 6,258,102 | B1 | 7/2001  | Pagedas |
| 6,264,663 | B1 | 7/2001  | Cano |

(Continued)

*Primary Examiner* — Mohamed G Gabr
(74) *Attorney, Agent, or Firm* — Carter, DeLuca & Farrell LLP

(57) ABSTRACT

A tissue specimen retrieval device includes an outer shaft including a proximal portion and a distal portion. The distal portion of the outer shaft includes a first jaw defining a first side of a lumen in the distal portion of the outer shaft. A second jaw defines a second side of the lumen in the distal portion of the outer shaft. The first and second jaws are actuatable between a closed configuration and an expanded configuration in which the first and second jaws are spaced relative to each other. A tissue specimen bag is supported by the first jaw and the second jaw. A bag brim of the tissue specimen bag defines a collapsed configuration when positioned in the lumen defined by the first jaw and the second jaw and an open configuration when the first and second jaws are in the expanded configuration.

20 Claims, 5 Drawing Sheets

(56) References Cited

U.S. PATENT DOCUMENTS

| | | | |
|---|---|---|---|
| 6,270,505 B1 | 8/2001 | Yoshida et al. |
| 6,280,451 B1 | 8/2001 | Bates et al. |
| 6,344,026 B1 | 2/2002 | Burbank et al. |
| 6,350,266 B1 | 2/2002 | White et al. |
| 6,350,267 B1 | 2/2002 | Stefanchik |
| 6,358,198 B1 | 3/2002 | Levin et al. |
| 6,368,328 B1 | 4/2002 | Chu et al. |
| 6,383,195 B1 | 5/2002 | Richard |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 * | 10/2004 | Shimm .............. A61B 17/3439 606/200 |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,654,283 B2 | 2/2010 | Seto et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinsk et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,542 B2 | 10/2016 | Hurley et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,624,638 B2 | 4/2017 | Lebreton et al. |
| 9,629,618 B2 | 4/2017 | Davis et al. |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 2017/0245839 A1 * | 8/2017 | Malkowski ......... A61B 17/3421 |

* cited by examiner

ACTUATION MECHANISMS FOR TISSUE SPECIMEN RETRIEVAL DEVICES AND TISSUE SPECIMEN RETRIEVAL DEVICES INCORPORATING THE SAME

FIELD

The present disclosure relates to tissue specimen retrieval from an internal body cavity and, more particularly, to articulation mechanisms for tissue specimen retrieval devices and tissue specimen retrieval devices incorporating the same to facilitate retrieval of a tissue specimen from the internal body cavity.

BACKGROUND

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment is highly desirable to inhibit seeding of cancer cells. Thus, with respect to breaking down large tissue specimens for retrieval through minimally-invasive openings, there is the added challenge of doing so within an enclosed environment.

SUMMARY

Provided in accordance with aspects of the present disclosure is a tissue specimen retrieval device including a housing and an outer shaft extending distally from the housing. The outer shaft includes a proximal portion and a distal portion. The outer shaft defines a lumen extending within the proximal portion and the distal portion of the outer shaft. The distal portion of the outer shaft includes a first jaw defining a first side of the lumen in the distal portion of the outer shaft. A second jaw defines a second side of the lumen in the distal portion of the outer shaft. The first and second jaws are actuatable between a closed configuration in which the first and second jaws define the lumen in the distal portion of the outer shaft, and an expanded configuration in which the first and second jaws are spaced relative to each other. A tissue specimen bag is supported by the first jaw and the second jaw. The tissue specimen bag includes a bag brim. The bag brim is removably coupled to the first jaw and the second jaw. The bag brim defines a collapsed configuration when positioned in the lumen defined by the first jaw and the second jaw and an open configuration when the first and second jaws are in the expanded configuration.

In an aspect of the present disclosure, the first jaw includes a first pivot point and a second pivot point and the second jaw defines a third pivot point and a fourth pivot point. Actuation of the first jaw and the second jaw between the closed configuration and the expanded configuration pivots the first jaw about the first and second pivot points and pivots the second jaw about the third and fourth pivot points to expand the bag brim between the closed configuration and the open configuration. The tissue specimen bag includes a bag body. The bag body is in a furled configuration when the first and second jaws are in the closed configuration. The bag body is in an unfurled configuration when the bag brim is in the open configuration.

In an aspect of the present disclosure, a first suture removably couples the bag brim to the first and second jaws. The bag brim includes a channel defined therein. A second suture extends within the channel formed in the bag brim. The second suture is configured to cinch the bag brim into a closed configuration. An actuator is positioned on the housing. The actuator is operably coupled to the second suture and configured to retract the second suture. The first and second jaws each include a plurality of orifices configured to receive the first suture therein to removably couple the bag brim to the first and second jaws.

In an aspect of the present disclosure, a first track is formed in a proximal portion of the first jaw. A second track is formed in a proximal portion of the second jaw. The first track overlaps the second track. A pin is positioned in the first track and the second track. Advancing the pin along a proximal to distal direction actuates the first and second jaws between the closed configuration and the expanded configuration. A driver is operably coupled to the pin and configured to advance the pin along the proximal to distal direction. An actuator is positioned on the housing. The actuator is operably coupled to the driver and configured to advance the driver along the proximal to distal direction.

In an aspect of the present disclosure, the housing includes a pistol-grip handle.

BRIEF DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Figure 1:
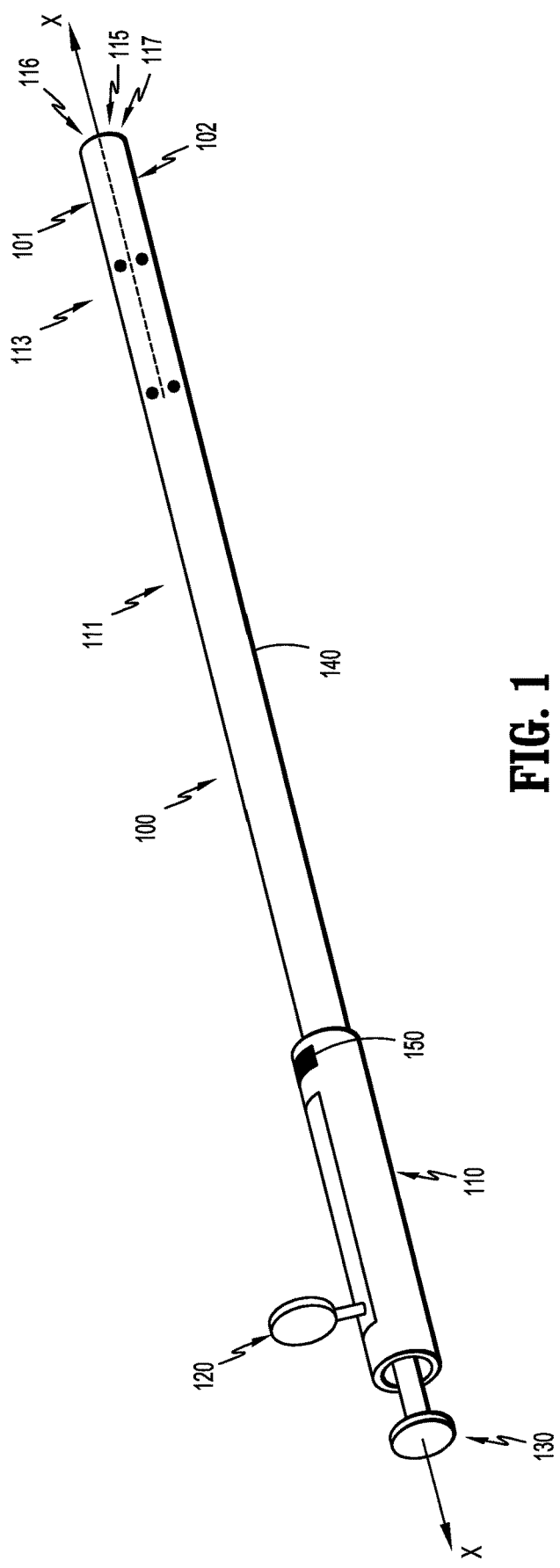
FIG. 1 is a side, perspective view of a tissue specimen retrieval device provided in accordance with aspects of the present disclosure, wherein the jaws of the tissue specimen retrieval device are in a closed configuration.

The present disclosure provides actuation mechanisms for tissue specimen retrieval devices and tissue specimen retrieval devices incorporating the same to facilitate retrieval of the tissue specimen from the internal body cavity. These and other aspects and features of the present disclosure are detailed below. As used herein, the term "distal" refers to the portion that is described which is further from a user, while the term "proximal" refers to the portion that is being described which is closer to a user. Further, any or all of the aspects and features described herein, to the extent consistent, may be used in conjunction with any or all of the other aspects and features described herein.

"About" or "approximately" or "substantially" as used herein may be inclusive of the stated value and means within an acceptable range of variation for the particular value as determined by one of ordinary skill in the art, considering the measurement in question and the error associated with measurement of the particular quantity (e.g., the limitations of the measurement system). For example, "about" may mean within one or more standard variations, or within ±30%, 20%, 10%, 5% of the stated value.

Descriptions of technical features or aspects of an exemplary embodiment of the disclosure should typically be considered as available and applicable to other similar features or aspects in another exemplary embodiment of the disclosure. Accordingly, technical features described herein according to one exemplary embodiment of the disclosure may be applicable to other exemplary embodiments of the disclosure, and thus duplicative descriptions may be omitted herein.

Exemplary embodiments of the disclosure will be described more fully below (e.g., with reference to the accompanying drawings). Like reference numerals may refer to like elements throughout the specification and drawings.

Referring to FIG. 1, a tissue specimen retrieval device provided in accordance with the present disclosure is shown generally identified by reference numeral 100. Tissue specimen retrieval device 100 includes a housing 110, first and second actuators 120, 130 operably associated with housing 110, an outer shaft 140 extending distally from housing 110, and an activation button 150. The outer shaft 140 includes a proximal portion 111 and a distal portion 113. The outer shaft 140 defines a lumen 115 extending within the proximal portion 111 and the distal portion 113 of the outer shaft 140.

Housing 110, although illustrated as defining a generally tubular configuration, may define any suitable configuration to facilitate grasping and manipulating tissue specimen retrieval device 100 such as, for example, a pencil-grip configuration, a pistol-grip configuration, etc., and may include any suitable features to enhance ergonomics such as, for example, recesses, protrusions, textured surfaces, finger rings, etc.

First actuator 120 is operably associated with housing 110 and is operably coupled to outer shaft 140 to enable selective actuation of the distal portion 113 of the outer shaft 140.

The first actuator 120 may be configured as a sliding actuator slidable along housing 110 (e.g., along longitudinal axis X-X), or may define any other suitable configuration such as, for example, a plunger actuator that is selectively manipulatable relative to housing 110 along a longitudinal axis of housing 110, a pivoting actuator pivotable relative to housing 110, etc.

Second actuator 130 is operably associated with housing 110 and coupled to a second suture 163 (see, e.g., FIGS. 2B and 3) to enable selective cinching of a brim 165 of tissue specimen bag 160. Second actuator 130 may be configured as a plunger actuator that is selectively manipulatable relative to housing 110, or may define any other suitable configuration such as, for example, a pivoting actuator pivotable relative to housing 110, a sliding actuator slidable along housing 110 (e.g., along longitudinal axis X-X), etc.

Referring to FIGS. 1 and 2A to 4B, the distal portion 113 of the outer shaft 140 includes a first jaw 101 defining a first side 116 of the lumen 115 in the distal portion 113 of the outer shaft 140. A second jaw 102 defines a second side 117 of the lumen 115 in the distal portion 113 of the outer shaft 140. The first and second jaws 101 and 102 are configured to be actuated between a closed configuration (see, e.g., FIG. 2A) in which the first and second jaws 101 and 102 define the lumen 115 in the distal portion 113 of the outer shaft 140, and an expanded configuration (see, e.g., FIG. 2B) in which the first and second jaws 101 and 102 are pivoted away from each other. A tissue specimen bag 160 is supported by the first jaw and the second jaw 101 and 102, respectively, and is positioned in the lumen 115 of the outer shaft 140 before the tissue specimen bag 160 is deployed by the first and second jaws 101 and 102. The tissue specimen bag 160 includes the brim 165. The brim 165 is removably coupled to the first jaw 101 and the second jaw 102. The brim 165 defines a collapsed configuration when positioned in the lumen 115 defined by the first jaw 101 and the second jaw 102 and an open configuration (see, e.g., FIG. 2B) when the first jaw 101 and the second jaw 102 are in the expanded configuration. The bag body 167 is in a furled configuration when the tissue specimen bag 160 is positioned in the lumen 115 of the outer shaft 140 before the tissue specimen bag 160 is deployed by the first and second jaws 101 and 102, respectively.

As an example, the proximal 111 and distal portions 113 of the outer shaft 140 may define approximately a 15 mm continuous tube when the distal portion 113 of the outer shaft 140 is in the closed configuration (e.g., before the tissue specimen bag 160 is deployed from the lumen 115 of the outer shaft 140).

The first jaw 101 includes a first pivot point 121 and a second pivot point 123 and the second jaw 102 defines a third pivot point 122 and a fourth pivot point 124. Actuation of the first jaw 101 and the second jaw 102 between the closed configuration and the expanded configuration pivots the first jaw 101 about the first and second pivot points 121 and 123 and pivots the second jaw 102 about the third and fourth points 122 and 124 to expand the brim 165 between the closed configuration and the open configuration. The tissue specimen bag 160 includes a bag body 167 (see, e.g., FIG. 5). As noted above, the bag body 167 is in a furled configuration when the first jaw 101 and the second jaw 102 are in the closed configuration. The bag body 167 unfurls from the brim 165 when the brim 165 is in the open configuration as a result of the actuation of jaws 101, 102.

Figure 2A:
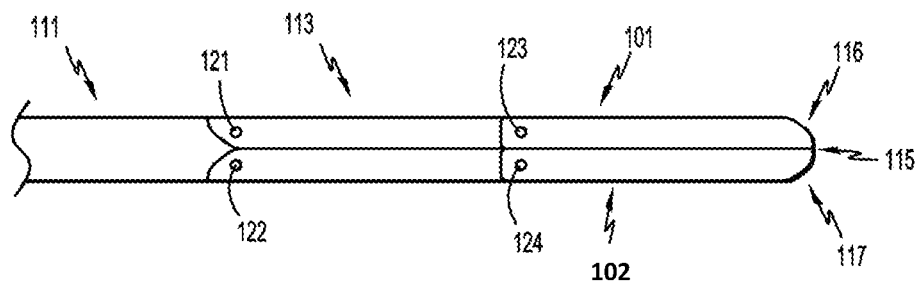
FIG. 2A is a top, plan view of the jaws of FIG. 1 in the closed configuration.
Figure 2B:
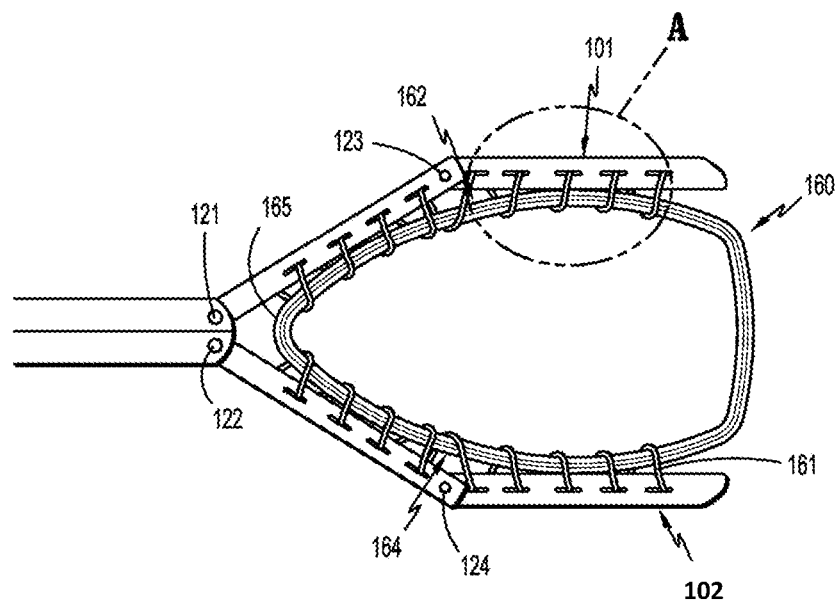
FIG. 2B is a top, plan view of the jaws of FIG. 1 in an expanded configuration and a tissue specimen bag in an open configuration.
Figure 3:
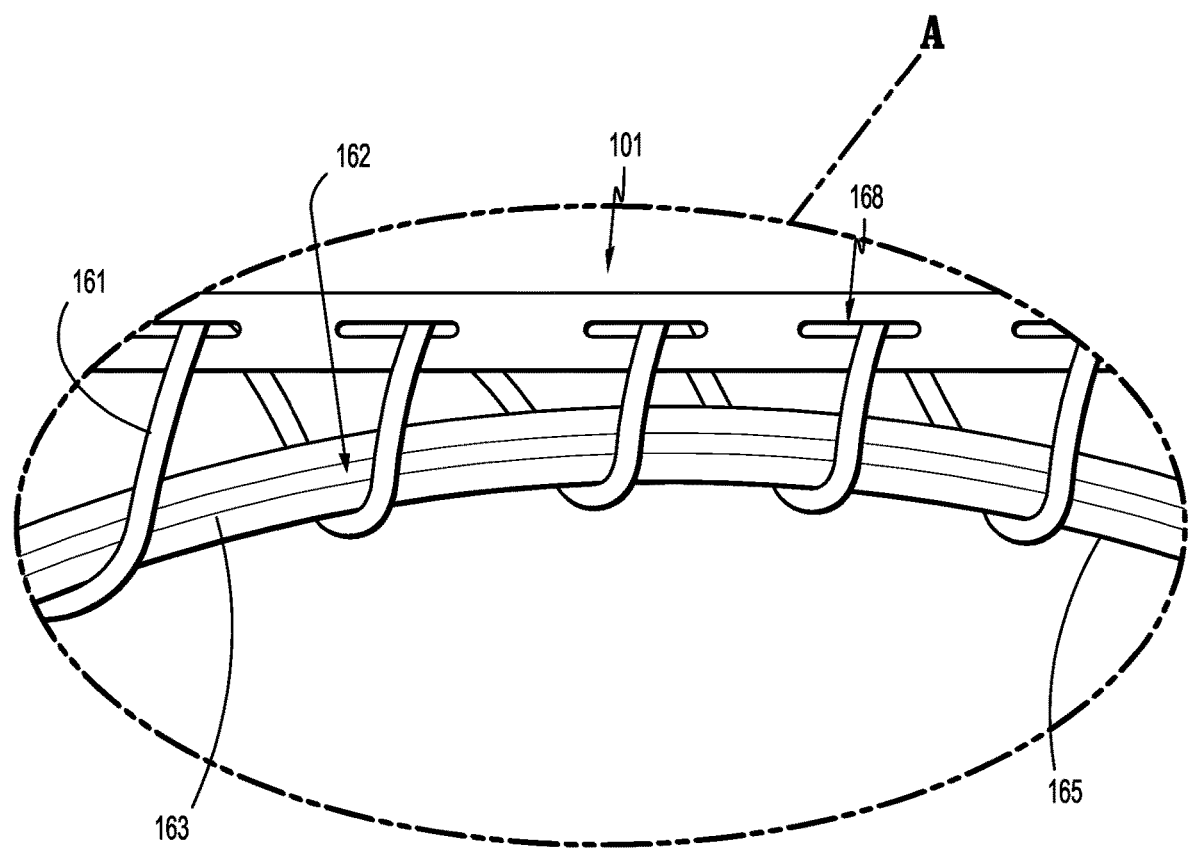
FIG. 3 is an enlarged, top, plan view of area "A" of FIG. 2B.

Referring particularly to FIGS. 2B and 3, a first suture 161 removably couples the brim 165 to the jaws 101, 102. The brim 165 includes at least one channel 162 formed therein. A second suture 163 extends within the channel 162 formed in the brim 165. The second suture 163 is configured to cinch the brim 165 into a closed configuration. The first jaw 101 and the second jaw 102 each include a plurality of orifices 168 configured to receive the first suture 161 therein to removably couple the brim 165 to the jaws 101, 102.

Tissue specimen bag 160 may be formed from any suitable bio-compatible material (or materials), e.g., ripstop nylon, configured to retain a tissue specimen "T" (FIG. 5) therein. Tissue specimen bag 160 defines at least one opening defined by brim 165, e.g., at open end 166 thereof, and includes one or more channels 162, 164 formed within brim 165 about open end 166 thereof for receipt of second suture 163, therein. The one or more channels 162, 164 may be separate or in communication with one another, and/or may extend about only a portion of open end 166 of tissue specimen bag 160 or about the entirety perimeter thereof. One or more of the openings of tissue specimen bag 160, e.g., open end 166, may include a cinch cord (e.g., second suture 163 extending through channels 162 and 164) disposed thereabout to enable selective closure of the opening. Tissue specimen bag 160 may be disengaged from jaws 101, 102 upon cinching closed open end 166 of tissue specimen bag 160, and cutting or separating of the first suture 161, using a separate instrument, e.g., grasping device, cutting device, and/or in any other suitable manner.

Figure 4A:
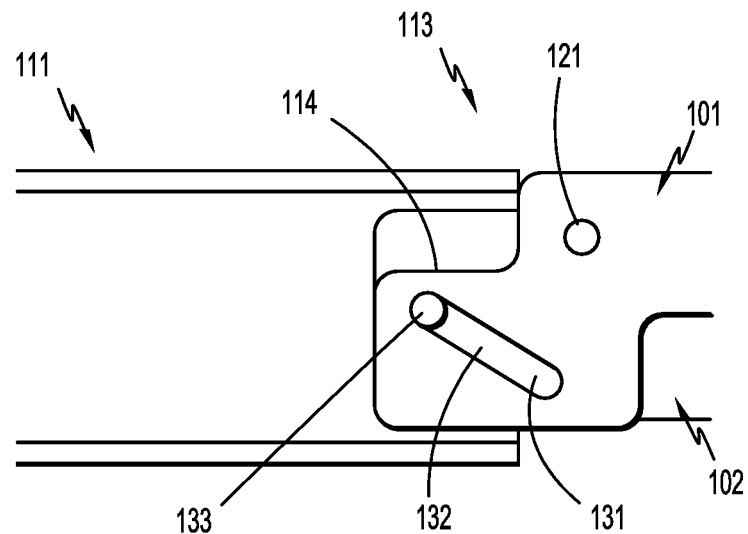
FIG. 4A is a top, plan view of an actuation mechanism of the jaws of FIG. 1 with the jaws in the closed configuration.
Figure 4B:
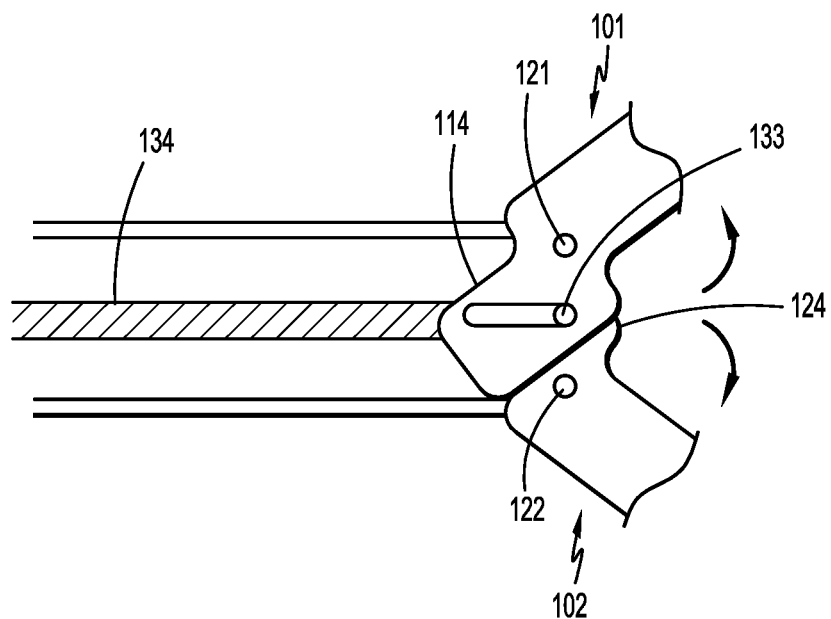
FIG. 4B is a top, plan view of the actuation mechanism of FIG. 4A with the jaws in the expanded configuration.

Referring particularly to FIGS. 1, 4A and 4B, a first track 131 is formed in a proximal end portion 114 of the first jaw 101. A second track 132 is formed in a proximal end portion 124 of the second jaw 102. The first track 131 overlaps the second track 132. A pin 133 is positioned in the first track 131 and the second track 132. Advancing the pin 133 along a proximal-to-distal direction (e.g., along longitudinal axis X-X in FIG. 1) actuates the jaws 101, 102 between the closed configuration and the expanded configuration. A driver 134 is operably coupled to the pin 133 and configured to advance the pin 133 along the proximal to distal direction. The first actuator 120 actuator is operably coupled to the driver 134 and configured to advance the driver 134 along the proximal to distal direction. The pin 133 may be locked in place but remain biased (e.g., by a spring) toward an actuated position, such the releasing the pin 133 causes actuation of the jaws 101,102. The pin 133 may be released by an activation button 150 to actuate the jaws 101,102.

Figure 5:
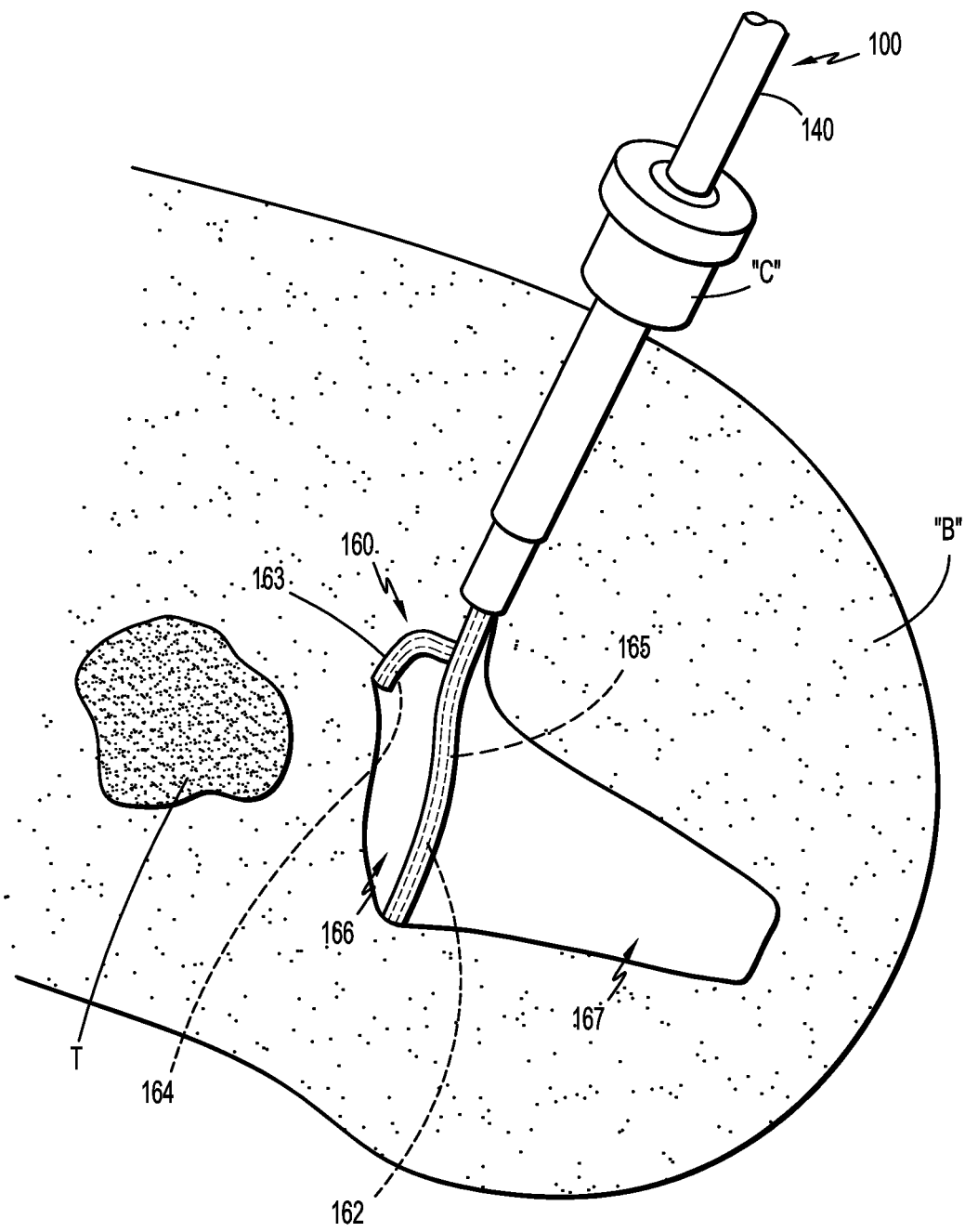
FIG. 5 is a perspective view of the tissue specimen retrieval device of FIG. 1 inserted through an access cannula into an internal body cavity for retrieval of a tissue specimen therefrom.

Continuing with reference to FIGS. 1 and 5, outer shaft 140 extends distally from housing 110, as noted above, and is configured for insertion through an access cannula "C" (FIG. 5) or natural passageway into an internal body cavity "B" (FIG. 5). Outer shaft 140 may be substantially rigid (within manufacturing tolerances and in response to reasonable loads applied thereto) or may include one or more portions configured to flex and/or articulate relative to a longitudinal axis thereof.

In use, the distal portion 113 of the outer shaft 140 is initially in the closed configuration to facilitate insertion of the distal portion 113 of the outer shaft 140 through an access cannula "C" (FIG. 5) or natural passageway into an internal body cavity "B" (FIG. 5). Once at least the distal portion 113 of the outer shaft 140 of tissue specimen retrieval device 100 is disposed within the internal body cavity "B" (FIG. 5), the jaws 101, 102 are actuated to the expanded configuration (see, e.g., FIGS. 2B and 4B) to expand the brim 165 to the open configuration (see, e.g., FIG. 2B). Thus, the distal portion 113 of the outer shaft 140 is used to deploy the tissue specimen bag 160 from the lumen 115 of the outer shaft 140 into the open configuration without the need for additional deployment arms. After a tissue specimen is placed in the tissue specimen bag 160, the first suture 161 can be cut to separate the brim 165 from the jaws 101,102. The brim 165 may be cinched by proximally pulling the second suture 165 (e.g., by pulling on second actuator 130) to close the open end 166 of the brim 165.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval device, comprising:
   a housing;
   an outer shaft extending distally from the housing and including a proximal portion and a distal portion, the outer shaft defining a lumen extending within the proximal portion and the distal portion of the outer shaft, the distal portion of the outer shaft including:
      a first jaw defining a first side of the lumen in the distal portion of the outer shaft;
      a second jaw defining a second side of the lumen in the distal portion of the outer shaft,
      the first and second jaws actuatable between a closed configuration in which the first and second jaws define the lumen in the distal portion of the outer shaft, and an expanded configuration in which the first and second jaws are spaced relative to each other; and
   a tissue specimen bag supported by the first jaw and the second jaw, the tissue specimen bag including a bag brim, the bag brim removably coupled to the first jaw and the second jaw, wherein the bag brim defines a collapsed configuration when positioned in the lumen defined by the first jaw and the second jaw and an open configuration when the first and second jaws are in the expanded configuration.

2. The tissue specimen retrieval device of claim 1, wherein the first jaw includes a first pivot point and a second pivot point and the second jaw defines a third pivot point and a fourth pivot point, and wherein actuation of the first jaw and the second jaw between the closed configuration and the expanded configuration pivots the first jaw about the first and second pivot points and pivots the second jaw about the third and fourth pivot points to expand the bag brim between the closed configuration and the open configuration.

3. The tissue specimen retrieval device of claim 2, wherein the tissue specimen bag further includes a bag body, the bag body being configured in a furled configuration when the first and second jaws are in the closed configuration, and being configured in an unfurled configuration when the bag brim is in the open configuration.

4. The tissue specimen retrieval device of claim 1, further including a first suture removably coupling the bag brim to the first and second jaws.

5. The tissue specimen retrieval device of claim 4, wherein the bag brim includes a channel defined therein and wherein a second suture extends within the channel formed in the bag brim, the second suture configured to cinch the bag brim into a closed configuration.

6. The tissue specimen retrieval device of claim 5, further including an actuator positioned on the housing, the actuator operably coupled to the second suture and configured to retract the second suture.

7. The tissue specimen retrieval device of claim 5, wherein the first and second jaws each include a plurality of orifices configured to receive the first suture therein to removably couple the bag brim to the first and second jaws.

8. The tissue specimen retrieval device of claim 1, further including:
   a first track formed in a proximal-portion of the first jaw;
   a second track formed in a proximal-portion of the second jaw, the first track overlapping the second track; and a pin positioned in the first track and the second track, wherein advancing the pin along a proximal-to-distal direction actuates the first and second jaws between the closed configuration and the expanded configuration.

9. The tissue specimen retrieval device of claim 8, further including a driver coupled to the pin and configured to advance the pin along the proximal-to-distal direction.

10. The tissue specimen retrieval device of claim 9, further including an actuator positioned on the housing, the actuator operably coupled to the driver and configured to advance the driver along the proximal-to-distal direction.

11. The tissue specimen retrieval device of claim 1, wherein the housing includes a pistol-grip handle.

12. A tissue specimen retrieval device, comprising:
an outer shaft including a proximal portion and a distal portion, the outer shaft defining a lumen extending within the proximal portion and the distal portion of the outer shaft, the distal portion of the outer shaft including:
 a first jaw defining a first side of the lumen in the distal portion of the outer shaft;
 a second jaw defining a second side of the lumen in the distal portion of the outer shaft,
 the first and second jaws actuatable between a closed configuration in which the first and second jaws define the lumen in the distal portion of the outer shaft, and an expanded configuration in which the first and second jaws are spaced relative to each other; and
a tissue specimen bag supported by the first jaw and the second jaw, the tissue specimen bag including a bag brim, the bag brim removably coupled to the first jaw and the second jaw, wherein the bag brim defines a collapsed configuration when positioned in the lumen defined by the first jaw and the second jaw and an open configuration when the first and second jaws are in the expanded configuration.

13. The tissue specimen retrieval device of claim 12, wherein the first jaw includes a first pivot point and a second pivot point and the second jaw defines a third pivot point and a fourth pivot point, and wherein actuation of the first jaw and the second jaw between the closed configuration and the expanded configuration pivots the first jaw about the first and second pivot points and pivots the second jaw about the third and fourth pivot points to expand the bag brim between the closed configuration and the open configuration.

14. The tissue specimen retrieval device of claim 13, wherein the tissue specimen bag further includes a bag body, the bag body being configured in a furled configuration when the first and second jaws are in the closed configuration, and being configured in an unfurled configuration when the bag brim is in the open configuration.

15. The tissue specimen retrieval device of claim 13, further including:
 a first track formed in a proximal portion of the first jaw;
 a second track formed in a proximal portion of the second jaw, the first track overlapping the second track; and
 a pin positioned in the first track and the second track, wherein advancing the pin along a proximal to distal direction actuates the first and second jaws between the closed configuration and the expanded configuration.

16. The tissue specimen retrieval device of claim 15, further including a driver coupled to the pin and configured to advance the pin along the proximal to distal direction.

17. The tissue specimen retrieval device of claim 12, further including a first suture removably coupling the bag brim to the first and second jaws.

18. The tissue specimen retrieval device of claim 17, wherein the bag brim includes a channel defined therein and wherein a second suture extends within the channel formed in the bag brim, the second suture configured to cinch the bag brim into a closed configuration.

19. The tissue specimen retrieval device of claim 18, wherein the second suture extends through the lumen in the proximal portion of the outer shaft, and wherein the second suture is connected with an actuator.

20. The tissue specimen retrieval device of claim 18, wherein the first and second jaws each include a plurality of orifices configured to receive the first suture therein to removably couple the bag brim to the first and second jaws.

* * * * *